(12) United States Patent
Perry et al.

(10) Patent No.: US 10,520,465 B2
(45) Date of Patent: Dec. 31, 2019

(54) GAS DETECTOR UTILIZING AN AQUEOUS SOLUTION

(71) Applicant: Carrier Corporation, Jupiter, FL (US)

(72) Inventors: Michael L. Perry, Glastonbury, CT (US); Robert M. Darling, South Windsor, CT (US)

(73) Assignee: CARRIER CORPORATION, Palm Beach Gardens, FL (US)

( * ) Notice: Subject to any disclaimer, the term of this patent is extended or adjusted under 35 U.S.C. 154(b) by 10 days.

(21) Appl. No.: 15/433,858

(22) Filed: Feb. 15, 2017

(65) Prior Publication Data

US 2017/0234829 A1 Aug. 17, 2017

Related U.S. Application Data

(60) Provisional application No. 62/296,262, filed on Feb. 17, 2016.

(51) Int. Cl.
*G01N 27/407* (2006.01)

(52) U.S. Cl.
CPC ..... *G01N 27/4077* (2013.01); *G01N 27/4075* (2013.01)

(58) Field of Classification Search
CPC .................. G01N 27/4077; G01N 27/4075
See application file for complete search history.

(56) References Cited

U.S. PATENT DOCUMENTS

| | | | |
|---|---|---|---|
| 3,878,080 A * | 4/1975 | Luck | G01N 27/4045 204/415 |
| 3,900,382 A | 8/1975 | Brown, Jr. | |
| 4,474,648 A | 10/1984 | Tantram et al. | |
| 4,627,906 A | 12/1986 | Gough | |
| 5,331,310 A * | 7/1994 | Stetter | G01N 27/4045 204/406 |
| 5,667,653 A | 9/1997 | Schneider et al. | |
| 5,906,726 A | 5/1999 | Schneider | |
| 6,319,473 B1 | 11/2001 | Ozaki et al. | |
| 6,746,587 B2 | 6/2004 | Saffell et al. | |
| 6,837,987 B1 | 1/2005 | King | |
| 7,022,213 B1 * | 4/2006 | Austen | G01N 27/404 200/264 |
| 7,156,968 B2 | 1/2007 | Tsapakh et al. | |
| 7,316,768 B2 | 1/2008 | Aldridge et al. | |
| 2003/0194351 A1 | 10/2003 | Tuomela | |
| 2009/0194417 A1 | 8/2009 | King | |
| 2013/0062223 A1 * | 3/2013 | Rabbett | G01N 27/4074 205/793 |

FOREIGN PATENT DOCUMENTS

| | | |
|---|---|---|
| CN | 103926277 A | 7/2014 |
| WO | 2013090015 A1 | 6/2013 |

OTHER PUBLICATIONS

Henderson, Robert E., "Using Electrochemical Sensors for Toxic Gas Measurement", Thermofisher, AET Buyers' Guide 2005, 2 pages.

* cited by examiner

*Primary Examiner* — J. Christopher Ball
(74) *Attorney, Agent, or Firm* — Cantor Colburn LLP

(57) ABSTRACT

A gas detection device including a vessel, wherein the vessel contains an aqueous solution, and a sensing element operably coupled to the vessel, wherein the sensing element is not in direct contact with the aqueous solution.

4 Claims, 2 Drawing Sheets

GAS DETECTOR UTILIZING AN AQUEOUS SOLUTION

CROSS-REFERENCE TO RELATED APPLICATION

The present application is a nonprovisional patent application, which claims priority to U.S. patent application Ser. No. 62/296,262, filed Feb. 17, 2016, which is herein incorporated in its entirety.

TECHNICAL FIELD OF THE DISCLOSED EMBODIMENTS

The presently disclosed embodiments generally relate to sensors for gas detection, and more particularly, to a gas detector utilizing an aqueous solution.

BACKGROUND OF THE DISCLOSED EMBODIMENTS

The lifetime of carbon monoxide sensors is usually limited by the amount of deionized water in the canister. Typically, the electrochemical cell in the sensor is required to be hydrated in order to properly function; however, the deionized water within the sensor is typically lost to the environment. Since carbon monoxide sensors are typically located in conditioned spaces, and HVAC systems are generally designed to maintain a relative humidity of approximately 40% to 60% within the conditioned space, there is a significant driving force for the removal of the deionized water within the carbon monoxide sensor. As such, the size of the water reservoir within the carbon monoxide sensor should be large enough to support loss of water vapor to the environment over the life of the sensor; however, to accomplish this task, the reservoir dominates the size of the carbon monoxide sensor. There is therefore a need for an improved carbon monoxide sensor that contains a smaller reservoir, but is capable of maintaining the hydration of the electrochemical cell for the life of the sensor.

SUMMARY OF THE DISCLOSED EMBODIMENTS

In one aspect, a gas detection device is provided. The gas detection device includes a vessel and a sensing element operably coupled to the vessel, wherein the vessel contains an aqueous solution; and the sensing element is not in direct contact with the aqueous solution. In an embodiment, the gas to be detected includes carbon monoxide.

In an embodiment, the aqueous solution is chosen from a group consisting of a concentrated salt solution and an acid aqueous solution. In an embodiment, the sensing device includes an electrochemical sensor.

In one embodiment, the vessel is formed from a plastic. In this embodiment, the sensing element includes a membrane electrode assembly, a first electrode operably coupled to the membrane electrode assembly, and a second electrode operably coupled to the membrane electrode assembly; wherein the membrane electrode assembly is disposed between the first electrode and the second electrode.

In another embodiment, the vessel is formed from a conductive metal. In this embodiment, the sensing element includes a membrane electrode assembly, and a first electrode operably coupled to the membrane electrode assembly. In this embodiment, a second electrode is operably coupled to an outer surface of the vessel.

DETAILED DESCRIPTION OF THE DISCLOSED EMBODIMENTS

Figure 1:
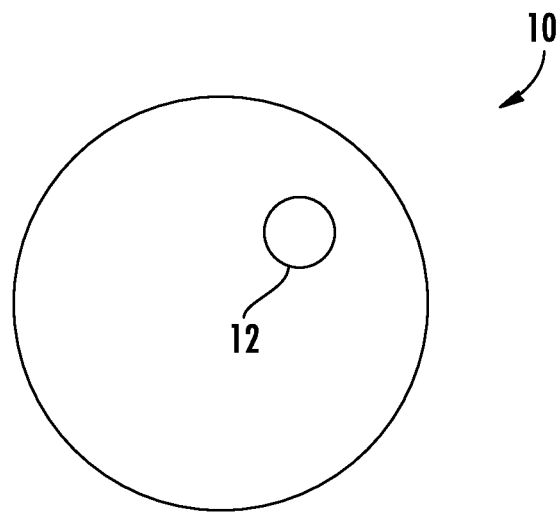
FIG. 1 illustrates a schematic diagram of a gas detector according to one embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Figure 2:
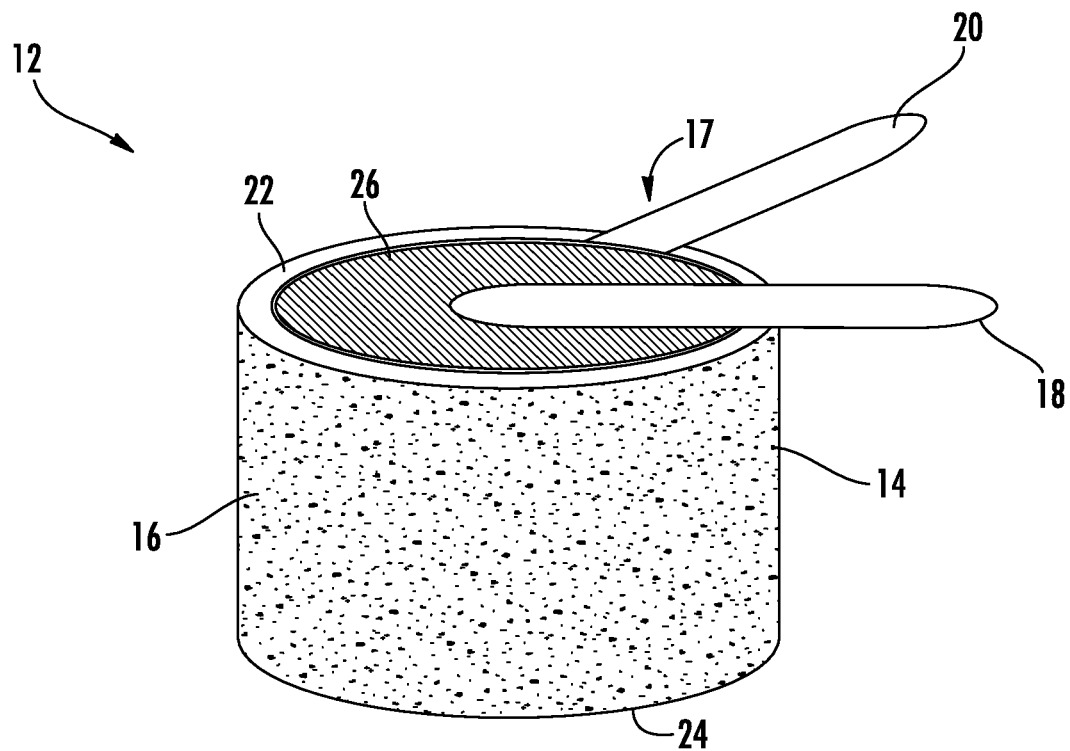
FIG. 2. Illustrates a schematic diagram of an electrochemical sensor for use in a gas detector according to one embodiment of the present disclosure.

FIG. 1 schematically illustrates an embodiment of a gas detection device, the gas detection device generally indicated at 10. In an embodiment, the gas detection device 10 is configured to detect carbon monoxide. The gas detection device 10 includes a sensor 12 disposed therein, wherein the sensor includes an electrochemical sensor. As shown in FIG. 2, the sensor 12 includes a vessel 14 configured to hold an aqueous solution 16. In one embodiment, the vessel 14 is formed from a plastic. In another embodiment, the vessel 14 is formed from a conductive metal. In an embodiment, the aqueous solution 16 is chosen from a group consisting of a concentrated salt solution and an acid aqueous solution, such as sodium chloride, lithium chloride, and sulfuric acid to name a few non-limiting examples.

There is net evaporation from an aqueous solution with a water activity greater than the relative humidity of its surroundings and a net absorption of water by an aqueous solution with a water activity less than the relative humidity of its surroundings. As such, the amount of water required may reduce more than the decrease in water volume, which can thereby reduce the volume of fluid necessary in the vessel 14. It will further be appreciated that the lower water activity of the selected concentrated salt solution or acid aqueous may improve the longevity of the sensor 12.

As shown in FIG. 2, the sensor 12 further includes a sensing element 17 operably coupled to the vessel 14. The sensing element includes a first electrode 18 a second electrode 20, and a membrane electrode assembly 26.

The membrane electrode assembly 26 is disposed between the first electrode 18 and the second electrode 20. The second electrode 20 is operably coupled to a top outer surface 22 of the vessel 14 and located adjacent to the aqueous solution 16. In embodiments where the vessel 14 is made from a conductive metal, the second electrode 20 may be operably coupled to any outer surface, for example the bottom outer surface 24, of the vessel 14. When the membrane electrode assembly 26 becomes hydrated from the aqueous solution 16, ions become highly mobile. The membrane electrode assembly 26 is an assembled stack of polymer electrolyte membrane (PEM) or alkali anion exchange membrane (AAEM) that allows the transport of the protons or hydroxide ions from the first electrode 18 to the second electrode 20 through the membrane electrode assembly 26 but forces the electrons to travel around a conductive path to the first electrode 18. The membrane electrode assembly 26 is not in direct contact with the aqueous solution in order to prevent flooding or degradation of the assembly 26. It will also be appreciated that the first electrode 18 and the second electrode 20 are not in direct contact with the aqueous solution to prevent corrosion of the first electrode 18 and the second electrode 20.

Figure 3:
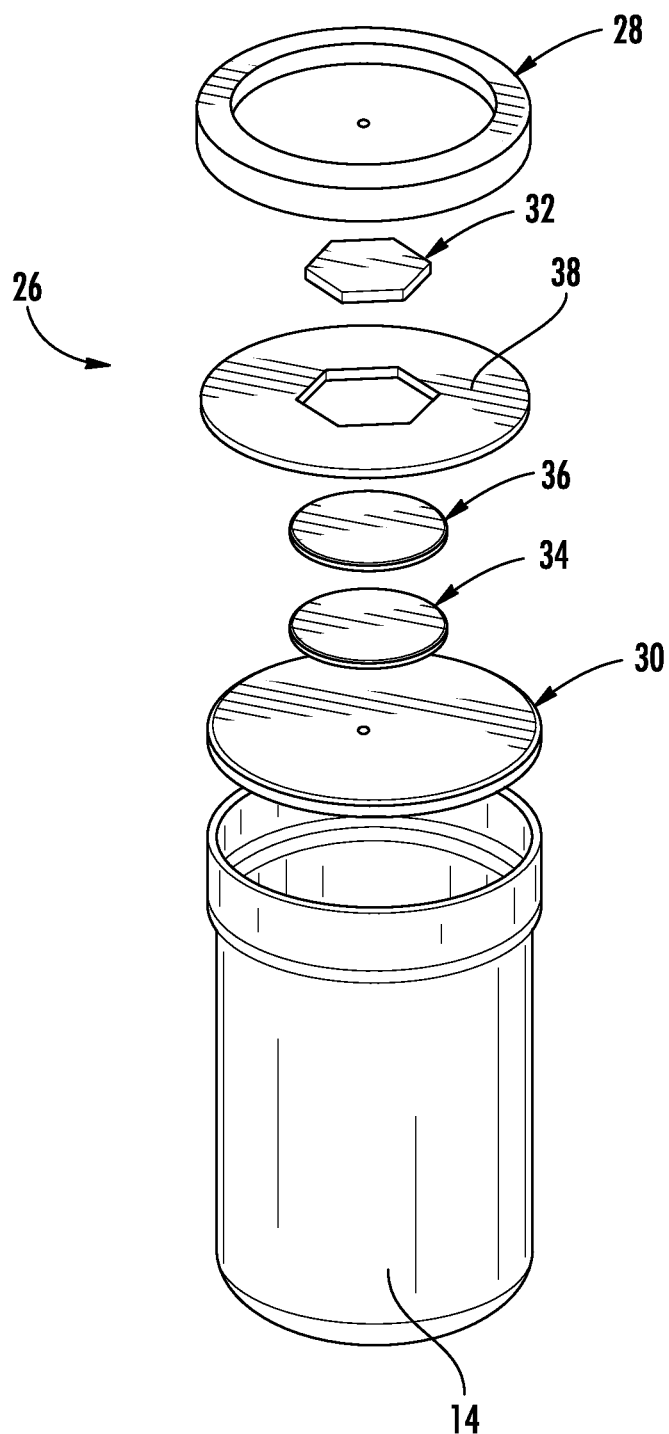
FIG. 3 illustrates a cross sectional view of a sensing element according to one embodiment of the present disclosure.

In some embodiments, as shown in FIG. 3, the membrane electrode assembly 26 includes a first gasket 28 and a second gasket 30, a first gas diffusion layer 32 and a second gas diffusion layer 34 disposed adjacent to the first gasket 28 and a second gasket 30, respectively. The first gas diffusion layer 32 and the second gas diffusion layer 34 are configured to ensure proper transport of gases, electrons, and heat of reaction. It will be appreciated that the first gas diffusion layer 32 and the second gas diffusion layer 34 may be a carbon paper (e.g., Toray paper to name one non-limiting example).

The membrane electrode assembly 26 further includes an ion exchange membrane 36 disposed adjacent to the second gas diffusion layer 34. In an embodiment, the ion exchange member includes a catalyst disposed thereon. The catalyst layers are typically composed of noble-metal catalyst, such as platinum or platinum-alloys, supported on carbon with an ionomer binder, which is the same polymeric material as the ion-exchange membrane. The ion exchange membrane promotes the transport of ions between a first catalyst layer and a second catalyst layer. The membrane electrode assembly 26 further includes a washer 38 disposed between the ion exchange membrane 36 and the first gas diffusion layer 32. It will be appreciated that the washer 38 is configured to separate the first gas diffusion layer 32 and the second gas diffusion layer 34 in order to reduce the likelihood of short-circuiting the cell since both are electrically conductive, and provides a good, solid surface for the rubber spacer on the top disk to sit and form an airtight seal, which prevents excess air exposed to the cell to name a couple of non-limiting examples.

In some embodiments, the membrane electrode assembly 26 may include a first catalyst layer (not shown) and a second catalyst layer (not shown) disposed adjacent to the first gas diffusion layer 32 and the second gas diffusion layer 34, respectively. The first gas diffusion layer 32 and the second gas diffusion layer 34 are further configured to distribute the reactants from gas flow channels uniformly along the active surface of the first catalyst layer and the second catalyst layer.

When toxic gas such as carbon monoxide (CO) comes in contact with the first electrode 18, oxidation of CO gas will occur on the first electrode 18 through chemical reaction with water molecules in the air. Connecting the first electrode 18 and the second electrode 20 through the membrane electrode assembly 26 allows ions (e.g. protons (H+)) generated on the first electrode 18 to flow toward the second electrode 20 through the membrane electrode assembly 26. In addition, generated electrons move to the second electrode 20 through the external wiring (not shown). The electrical characteristic measured across the first electrode 18 and the second electrode 20 may be used to determine whether to alert the user of potentially dangerous levels of carbon monoxide.

Moreover, calibration of the controls of the sensor may be required due to using an aqueous solution in lieu of water. The use of an aqueous solution nominally increases the electrical resistance across the membrane electrode assembly 26; thus, the controls for detecting CO need to be adjusted accordingly to accommodate for the lower water activity of the aqueous solution. For example, an alert may be given at an electrical characteristic measurement of 5 mA using water, whereas an alert may be given at an electrical characteristic measurement of 4 mA using an aqueous solution.

It will therefore be appreciated that the present carbon monoxide detector 10 uses a vessel 14 containing an aqueous solution 16 to substantially reduce the size of the vessel 12 without negatively impacting the life of the gas detection device 10.

While the disclosure has been illustrated and described in detail in the drawings and foregoing description, the same is to be considered as illustrative and not restrictive in character, it being understood that only certain embodiments have been shown and described and that all changes and modifications that come within the spirit of the disclosure are desired to be protected.

What is claimed is:

1. A gas detection device configured to detected a gas, the gas detection device comprising:
   a vessel, wherein the vessel contains an aqueous solution; and
   a sensing element operably coupled to the vessel, wherein the sensing element is not in direct contact with the aqueous solution;
   wherein the aqueous solution is chosen from a group consisting of a concentrated salt solution and an acid aqueous solution;
   wherein the sensing element comprises:
   a membrane electrode assembly;
   a first electrode operably coupled to the membrane electrode assembly; and
   a second electrode operably coupled to the membrane electrode assembly;
   wherein the membrane electrode assembly is disposed between the first electrode and the second electrode;
   wherein the vessel comprises a conductive metal;
   wherein the second electrode is operably coupled to an outer surface of the vessel.

2. The gas detection device of claim 1, wherein the sensing element comprises an electrochemical sensor.

3. The gas detection device of claim 1, wherein the gas to be detected comprises carbon monoxide.

4. A gas detection device comprising:
   a vessel, wherein the vessel contains an aqueous solution; and
   a sensing element operably coupled to the vessel, wherein the sensing element is not in direct contact with the aqueous solution;
   wherein the vessel comprises a conductive metal;
   wherein the sensing element comprises:
   a membrane electrode assembly positioned at a top of the vessel;
   a first electrode operably coupled to the membrane electrode assembly;
   a second electrode operably coupled to a bottom outer surface of the vessel.

* * * * *